US011344389B2

(12) United States Patent
Freiwald et al.

(10) Patent No.: US 11,344,389 B2
(45) Date of Patent: May 31, 2022

(54) ARRANGEMENT COMPRISING AN ABUTMENT POST AND AN APPURTENANT CAP, AS WELL AS A TOOL FOR APPLICATION OF THE CAP

(71) Applicant: Dentsply Implants Manufacturing GmbH, Hanau (DE)

(72) Inventors: Florian Freiwald, Babenhausen (DE); André Maack, Neustadt a.d. Weinstraße (DE); Marco Degidi, Bologna (IT)

(73) Assignee: Dentsply Implants Manufacturing GmbH, Hanau (DE)

( * ) Notice: Subject to any disclaimer, the term of this patent is extended or adjusted under 35 U.S.C. 154(b) by 210 days.

(21) Appl. No.: 16/464,737

(22) PCT Filed: Nov. 28, 2017

(86) PCT No.: PCT/EP2017/001382
§ 371 (c)(1),
(2) Date: May 29, 2019

(87) PCT Pub. No.: WO2018/099594
PCT Pub. Date: Jun. 7, 2018

(65) Prior Publication Data
US 2019/0307535 A1    Oct. 10, 2019

(30) Foreign Application Priority Data

Dec. 1, 2016 (DE) ..................... 10 2016 123 285.8

(51) Int. Cl.
*A61C 8/00*    (2006.01)
(52) U.S. Cl.
CPC ............ *A61C 8/0069* (2013.01); *A61C 8/005* (2013.01); *A61C 8/0048* (2013.01); *A61C 8/0089* (2013.01); *A61C 8/0062* (2013.01)

(58) Field of Classification Search
CPC ..... A61C 8/0069; A61C 8/0048; A61C 8/005; A61C 8/0089; A61C 8/0062; A61C 8/0007; A61B 17/92
(Continued)

(56) References Cited

U.S. PATENT DOCUMENTS 4,681,542 A    7/1987 Baum
4,850,870 A    7/1989 Lazzara et al.
(Continued)

FOREIGN PATENT DOCUMENTS

CN    105434007 A    3/2016
CN    205715413 U    11/2016
(Continued)

OTHER PUBLICATIONS

Eriberto Bressan et al, Experimental and computational investigation of Morse taper conometric system reliability for the definition of fixed connections between dental implants and prostheses, Proceedings of the Institution of Mechanical Engineers, Part H: Journal of Engineering in Medicine published online Jul. 23, 2014.
(Continued)

*Primary Examiner* — Matthew M Nelson
(74) *Attorney, Agent, or Firm* — Katterle Nupp LLC; Paul Katterle; Robert Nupp

(57) ABSTRACT

An arrangement for mounting to a dental implant and a tool for use therewith. The arrangement includes an abutment post connected to a conical cap. The abutment post has a conical section with a conical outer surface configured to be complementary to a conical inner surface of a conical recess of the conical cap in such a manner that the conical cap can be placed on the conical section so as to at least partially receive the conical section in its conical recess. The inner surface of the conical cap and the outer surface of the abutment post are inclined relative to one another in such a
(Continued)

manner that the conical cap can be connected to the abutment post by friction locking between the inner surface and the outer surface. The conicity of the conical section differs from the conicity of the conical recess.

18 Claims, 10 Drawing Sheets

(58) Field of Classification Search
USPC ........................................................ 433/172
See application file for complete search history.

(56) References Cited

U.S. PATENT DOCUMENTS

| | | | |
|---|---|---|---|
| 6,974,322 B2 | 12/2005 | May | |
| 7,402,040 B2 | 7/2008 | Turri | |
| 9,982,733 B2 | 5/2018 | Shih | |
| 10,610,337 B2* | 4/2020 | Degidi | A61C 8/005 |
| 2004/0209226 A1* | 10/2004 | Rogers | A61C 13/0001 |
| | | | 433/173 |
| 2004/0209227 A1* | 10/2004 | Porter | A61C 8/0069 |
| | | | 433/173 |
| 2008/0032263 A1* | 2/2008 | Bondar | A61C 8/005 |
| | | | 433/173 |
| 2010/0151420 A1* | 6/2010 | Ranck | A61C 8/0012 |
| | | | 433/173 |
| 2011/0014588 A1* | 1/2011 | Seavey | A61C 8/0059 |
| | | | 433/174 |
| 2011/0306014 A1* | 12/2011 | Conte | A61C 8/005 |
| | | | 433/173 |
| 2012/0270180 A1* | 10/2012 | Dahlstrom | A61C 8/0068 |
| | | | 433/173 |
| 2013/0089834 A1* | 4/2013 | Fromovich | A61C 8/0024 |
| | | | 433/174 |
| 2013/0260336 A1* | 10/2013 | Bondar | A61C 8/005 |
| | | | 433/173 |
| 2014/0045145 A1* | 2/2014 | Buchegger | A61C 8/0069 |
| | | | 433/201.1 |
| 2014/0170597 A1* | 6/2014 | Honig | A61C 8/0068 |
| | | | 433/173 |
| 2014/0242550 A1* | 8/2014 | Degidi | A61C 13/20 |
| | | | 433/201.1 |
| 2014/0370459 A1* | 12/2014 | Hurson | A61C 8/0068 |
| | | | 433/173 |
| 2016/0113739 A1* | 4/2016 | Honig | A61C 8/0074 |
| | | | 433/173 |
| 2017/0007375 A9* | 1/2017 | Fromovich | A61C 8/0025 |
| 2017/0258558 A1* | 9/2017 | Morgan | A61C 8/0048 |

FOREIGN PATENT DOCUMENTS

| | | | |
|---|---|---|---|
| DE | 20121617 U1 | 3/2003 | |
| DE | 102011000960 B4 * | 7/2019 | ......... A61C 8/0075 |
| EP | 0574658 A1 | 3/1993 | |
| EP | 1086662 A2 | 3/2001 | |
| EP | 1704829 A1 | 9/2006 | |
| FR | 2861982 | 5/2005 | |
| WO | WO9605769 A1 | 2/1996 | |
| WO | WO-9952466 A1 * | 10/1999 | ......... A61C 8/0068 |
| WO | WO9952466 A1 | 10/1999 | |
| WO | WO2018099594 A3 | 6/2018 | |

OTHER PUBLICATIONS

International Preliminary Report on Patentability for corresponding PCT application (PCT/EP2017/001382).

* cited by examiner

ARRANGEMENT COMPRISING AN ABUTMENT POST AND AN APPURTENANT CAP, AS WELL AS A TOOL FOR APPLICATION OF THE CAP

CROSS-REFERENCE TO RELATED APPLICATION(S)

This application is the U.S. national phase of PCT Application No. PCT/EP2017/001382 filed on Nov. 28, 2017, which claims priority to German Patent Application No. 10 2016 123 285.8 filed on Dec. 1, 2016, the disclosures of which are incorporated in their entirety by reference herein.

TECHNICAL FIELD

The disclosure relates to an arrangement for positioning in and/or on a dental implant, and a tool for applying a conical cap to an abutment post.

BACKGROUND

Already known from EP 1 086 662 B1 is an arrangement for positioning in an implant. The implant comprises a dental implant which is suitable for being anchored in a jawbone of a patient.

The known arrangement comprises an abutment post and a conical cap which can be connected to this.

The abutment post has a conically running section, the conically running outer surface of which is configured to be complementary to a conically running inner surface of a conically running recess of conical cap in such a manner that the conical cap can be placed on the section and receives this at least in certain areas.

This prior-art conical cap is received in a dental prosthesis and fixed inside the dental prosthesis with a self-curing plastic. The conical cap together with the dental prosthesis is then placed on the abutment post.

It is disadvantageous here that self-curing plastics must be used and processed. It is also disadvantageous that the dental prosthesis must be filled with the plastic in a suitable manner in order to fix the conical cap so that this sits correctly on the abutment post in the end state. The plastic must be filled in from the side of the dental prosthesis in a time-consuming manner.

All these steps are necessary in order to ensure a problem-free loading of the conical cap, in particular during chewing.

It is therefore desirable to position a conical cap in a correct position on an abutment post with as few working steps as possible and connect the conical cap to this abutment post as permanently and loadably as possible.

SUMMARY

In accordance with the disclosure, an arrangement is provided for positioning in and/or on an implant. The arrangement includes an abutment post connected to a conical cap. The abutment post has a conical section with a conical outer surface configured to be complementary to a conical inner surface of a conical recess of the conical cap in such a manner that the conical cap can be placed on the conical section so as to at least partially receive the conical section in its conical recess. The inner surface of the conical cap and the outer surface of the abutment post are inclined relative to one another in such a manner that the conical cap can be connected to the abutment post by a friction locking between the inner surface and the outer surface in a tension-resistant and/or captive and/or safe-to-chew manner. The conicity of the conical section differs from the conicity of the conical recess.

BRIEF DESCRIPTION OF THE DRAWINGS

The features, aspects, and advantages of the present disclosure will become better understood with regard to the following description, appended claims, and accompanying drawings where:

DETAILED DESCRIPTION OF ILLUSTRATIVE EMBODIMENTS

Figure 1:
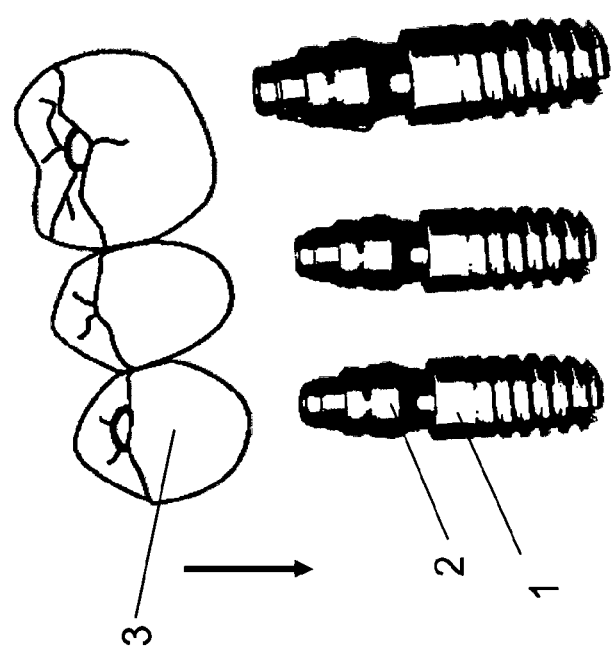
FIG. 1 shows three implants which are each connected to an abutment post of the type described here and artificial teeth which are provided to be connected to the implants.

According to the disclosure, it has been identified that the inner surface of the conical cap and the outer surface of the abutment post must be inclined relative to one another in such a manner that the conical cap can be connected to the abutment post by a frictional locking between the inner surface and the outer surface in a tension-resistant and/or captive and/or safe-to-chew manner.

Specifically, it has been identified that the conicity of the conically running section must differ from the conicity of the conically running recess in order to make a firm connection. Conicity is understood as the change in the diameter in the case of a conically running structure or in the case of a cone in the direction of the axis of symmetry of the cone or the conicity.

It has surprisingly been found that a frictional locking is sufficient to connect the conical cap so firmly, in particular in a tension-resistant manner, to the abutment post that this sits captively and in a safe-to-chew manner thereon.

Particularly surprisingly, the arrangement can be used when replacing incisors and molars. The arrangement can furthermore be used in treatments which require an immediate loading of the arrangement and in treatments which allow a delayed loading of the arrangement.

The conical cap could exclusively be connectable or connected to the abutment post by frictional locking in a tension-resistant and/or captive and/or safe-to-chew manner, wherein no means are provided which connect the conical cap to the abutment post by an adhesive bond and/or form fit. By this means it is possible to completely dispense with screws and/or adhesives by means of which a connection could be made between the conical cap and the abutment post. Thus, time and working steps can be saved for the processing of plastics or screws.

The conically running outer surface of the structure could enclose with the axis of symmetry of its conicity a first angle of inclination in the range of 1° to 8°, preferably in the range of 2° to 7°, particularly preferably in the range of 4° to 6° and the conically running inner surface could enclose with the axis of symmetry of its conicity a second angle of inclination in the range of 1° to 8°, preferably in the range of 2° to 7°, particularly preferably in the range of 4° to 6° wherein the first angle of inclination is greater than or smaller than the second angle of inclination. These ranges have proved particularly suitable for making a firm frictional locking.

Against this background, the first angle of inclination could be 5.8°. This value results in a high tensile strength of the connection between conical cap and abutment post. Furthermore, with the choice of this angle of inclination, the conical cap can strike or press particularly well onto the abutment post as a result of a pulse action.

The frictional locking could take place in a lower region of the conical cap which faces the opening of the conical cap. By this means, means can be provided in an upper region of the conical cap which ensure a correct and permanent seat of the conical cap.

Against this background, the frictional locking between the abutment post and the conical cap can be released by a tensile force which lies in the range of 2 N to 80 N, preferably in the range of 20 N to 80 N, particularly preferably in the range of 20 N to 40 N. These ranges are particularly suitable for producing chewing safety.

During application of the tensile force, the abutment post is held firmly and the conical cap is moved relative to this by pulling on the conical cap with the tensile force.

The frictional locking between the abutment post and the conical cap could be released by a tensile force in the amount of 30 N. This tensile force is sufficiently high to withstand usually high tensile forces in the mouth, for example when chewing caramel sweets. Furthermore, the conical cap is fixed sufficiently firmly for a patient but can be released again by a doctor or trained personnel.

A first lateral force locking device can be provided on the abutment post and a second lateral force locking device can be provided in and/or on the conical cap. By this means, a tilting of the conical cap relative to a longitudinal axis of the abutment post and/or the conical cap is prevented when lateral forces or bending moments act on the conical cap placed thereon. Such forces or bending moments can be applied by the tongue of the patient.

The first lateral force locking device can be configured as a cylindrical section or cylindrical connector with a free upper end. A cylindrical section is relatively easy to fabricate and provides sufficiently good stabilization against tilting.

The second lateral force locking device can be configured as a cylindrical section or cylindrical cavity with a closed upper end. By this means it is possible to receive the first lateral locking device. In this respect, the second lateral locking device is configured to be complementary to the first.

A first anti-twisting device can be provided on the abutment post and a second anti-twisting device can be provided in and/or on the conical cap. This avoids the cap twisting or rotating relative to the abutment post.

The first anti-twisting device can be configured, at least in sections, as a multi-sided or polygonal prism. A prism has non-inclined surfaces and can thus support the lateral force locking devices by stabilizing against tilting moments. The prism further prevents any twisting of the conical cap relative to the abutment post.

The second anti-twisting device can be configured as a multi-sided or polygonal cavity. As a result, it is possible to receive the first anti-twisting device. In this respect, the second anti-twisting device is configured to be complementary to the first.

The conical cap can have a solid pin projecting from the tip on the tip thereof. By this means the arrangement can be connected to other arrangements, for example, by means of weld wire. By this means several conical caps could be stabilized in their positions relative to their abutment posts.

The conical cap could have only one opening, namely for receiving the abutment post. This avoids impurities entering between the conical cap and the abutment post. This can occur if openings are provided for screws or for filling of plastics. The head end of the abutment post is closed or sealed by the hood like and closed conical cap.

The conical cap could have an external thread, eversions or other raised structures. This makes it possible to connect suprastructures to the conical cap. Specifically it is feasible to adhesively bond an artificial tooth to the conical cap.

The arrangement described here could preferably be fastened in and/or on an isolated implant, which is not connected to other implants by artificial connecting means. A single crown can be fixed by this means. Furthermore, the arrangement could be provided on several implants, for example in order to fix a bridge. The arrangement can be used to replace incisors and/or molars.

A stop and/or no gap could be formed axially between the conical cap and the abutment post. As a result of the stop, a conical cap comes to abut against the distal end of the abutment post in a stable and defined position without a gap remaining distally between stop and conical cap. In particular, the stop ensures that the conical cap is not pressed too firmly onto the abutment post but in a defined manner. The conical cap can therefore be released again by the dentist when this is necessary.

An abutment post with a stop or a conical cap with a stop could be used in an arrangement of the type described here. The stop can be assigned to the abutment post or formed in one piece with this. The stop can be arranged inside the conical cap or formed in one piece with this.

In this respect, a conical cap with a stop can be provided as an individual part in order to be connected detachably again to a suitable counter piece. In addition, an abutment post with a stop can be provided as an individual part in order to be connected detachably again to a suitable counter piece.

The object mentioned initially is also solved by a tool for application of a conical cap to an abutment post, comprising a handle for holding the tool and a device for applying a force or an impulse to the conical cap.

The device comprises a flat or rounded striking surface for abutment against the conical cap in order to produce a friction locking between the conical cap and the abutment post, so that these are connected to one another in a tension-resistant and/or captive and/or safe-to-chew manner.

The striking surface and the acting forces and impulses are configured so that a conical cap is connected detachably again to an abutment post.

The striking surface could be configured to be not pointed in the direction of the conical cap. This avoids damage to the conical cap. Furthermore, the conical cap is exposed to force or impulse over a large area.

The striking surface could be assigned to a striking element of the device, wherein the striking element is movable relative to a housing and/or to the handle in order to initially tension at least one spring and release it again by further movement. The striking surface or the striking element can thus be placed simply on the conical cap and pressed against this in order to initially tension a spring and then release it again.

Further triggering mechanisms which must be operated by hand are not necessary and preferably not provided.

A nutating element could be provided which is tiltable relative to the longitudinal axis of the device and/or the direction of movement of a spring-loaded hammer and/or the striking element in order to move a hammer initially against the force of a first spring during movement of the striking element. The nutating element presses the hammer against the first spring in a skew position and tensions the first spring.

When aligned parallel to the longitudinal axis or to the direction of movement, the nutating element could dip into a recess of the hammer and thereby release the first spring in such a manner that this moves the hammer in the direction of the striking surface. As soon as the nutating element dips into the recess, the hammer lacks a counter bearing so that the first spring can accelerate the hammer by relaxing.

The first spring could be provided between the handle or the housing and the hammer. A second spring could also be provided for the spring loading of the nutating element. As a result of the spring loading, the nutating element is relatively well stabilized when this presses against the hammer.

A set could comprise an arrangement of the type described here and a tool of the type described here. In addition to the tool, the set could also additionally or alternatively to the arrangement comprise at least one isolated abutment post with a stop and/or additionally an isolated conical cap with a stop. Thus, a dentist or another person can connect the conical caps described here with the abutment posts described here in a defined and medically suitable manner. A medically suitable release of the conical caps from the abutment post is ensured if required.

FIG. 1 shows three implants 1 which are each connected to an abutment post 2 of the type described here, and three artificial teeth 3. The teeth 3 are provided to be connected to the three implants 1 when the implants 1 are anchored in a jaw.

The implants 1 shown have an external thread which faces the apical end. However, other types of implants from those shown here can also be used in order to be connected to the abutment post 2. The teeth 3 are placed in the implants 1 in the direction of the arrow.

Three connected teeth 3 are shown here which serve as a bridge and stabilize the relative positions of the implants 1 and their appurtenant components with respect to one another. This is associated with the fact that the teeth 3 are connected to the jaw bone at several points and therefore have almost no freedom of movement.

However, it is specifically feasible to implant a free-standing implant 1 which should only bear a single tooth, without further artificial connecting means to other implants 1 and combine with an arrangement of the type described here.

Figure 2:
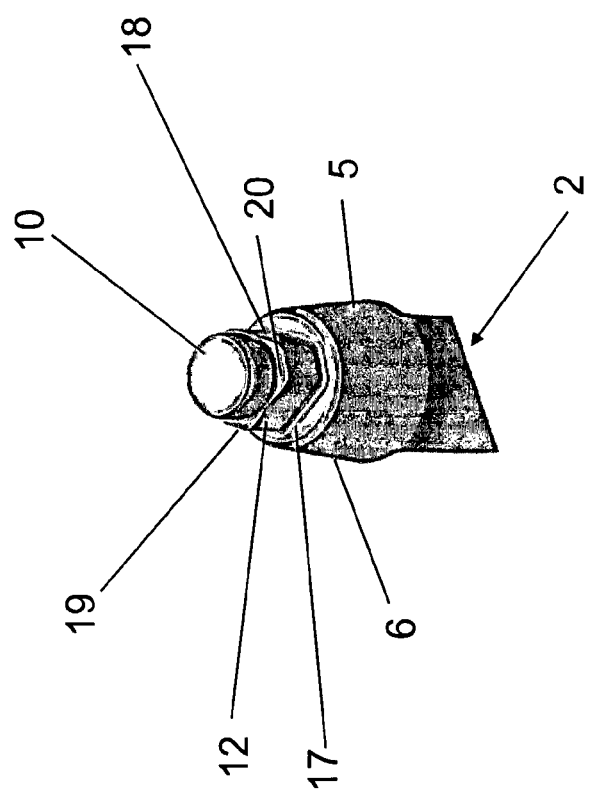
FIG. 2 shows a perspective view in sections of the upper part of an abutment post described here which projects from an implant and can be connected to the conical cap.
Figure 3:
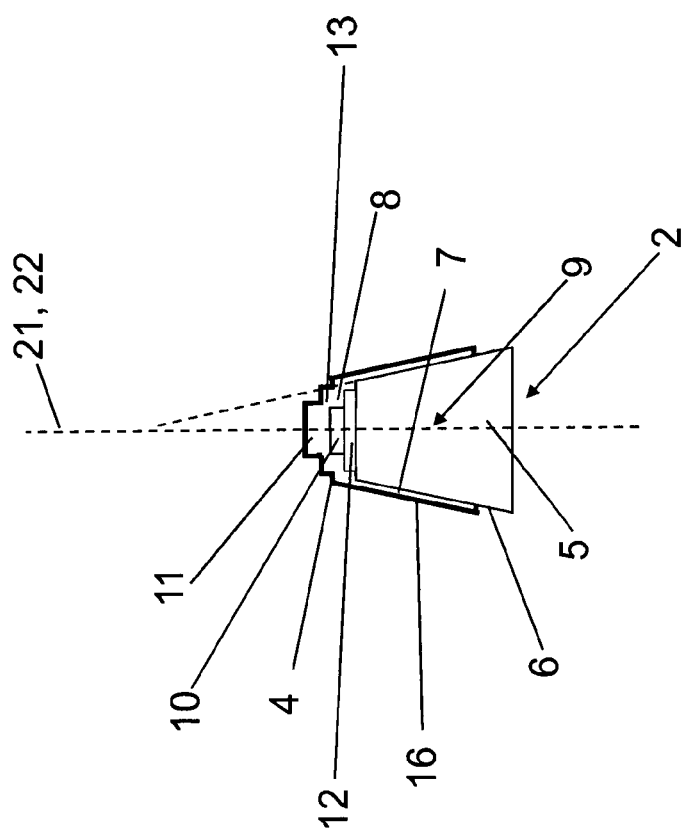
FIG. 3 shows a schematic sectional view of an arrangement which comprises an abutment post of the type described here and a conical cap of the type described here, wherein only the upper part of the abutment post is shown schematically.
Figure 4:
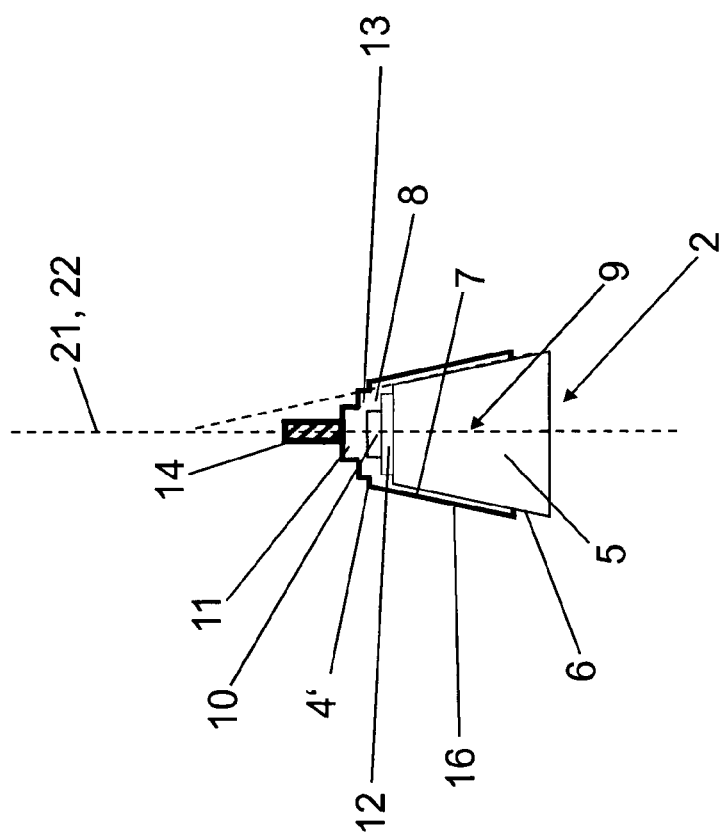
FIG. 4 shows a schematic sectional view of an arrangement, which comprises an abutment post of the type described here and a conical cap of the type described here, wherein the conical cap has a solid pin which projects with a free end from the tip thereof in the direction of the longitudinal axis of the abutment post in order to be welded to a weld wire.
Figure 5:
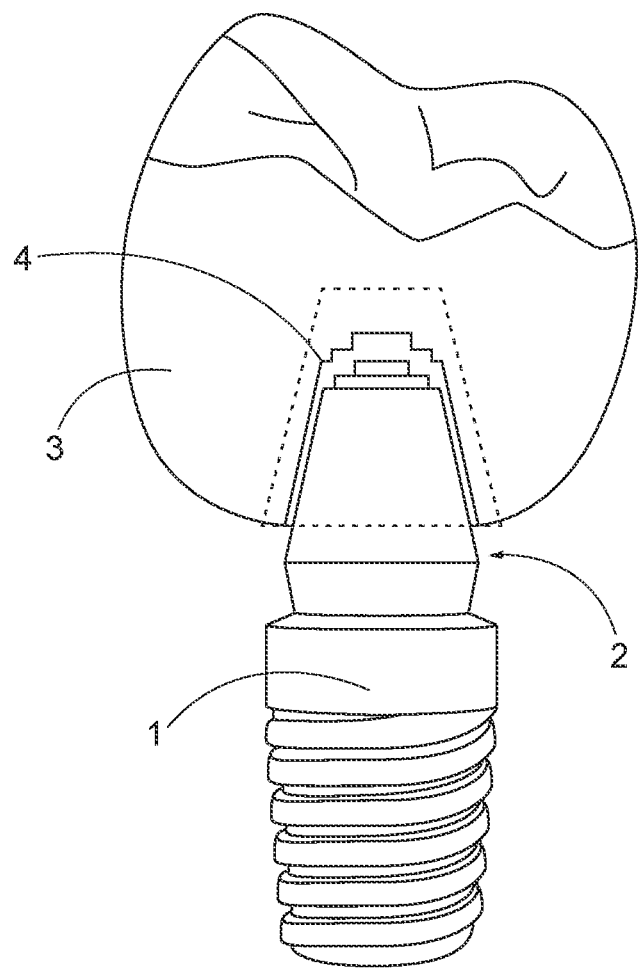
FIG. 5 shows a schematic view of an isolated implant in which an arrangement of the type described here can be anchored, wherein the arrangement can be connected to a single tooth and wherein the tooth can be connected to a conical cap which is only fixed by frictional locking on the abutment post of the implant implanted in the jaw.

FIG. 2 shows a perspective view in sections of the part of the abutment post 2 described here, which projects from the interior of the implant 1 and is to be connected to a conical cap 4 according to FIGS. 3 to 5.

FIG. 3 shows in a schematic sectional view an arrangement for positioning in an implant not shown. The lower part of the abutment post 2, which is connected to an implant not shown, is also not shown and can be configured in many respects to be connected to an implant. The abutment post 2 can, for example, also be configured to be angled.

The arrangement comprises an abutment post 2 and a conical cap 4 which can be connected or is connected to this. The abutment post 2 has a conically running section 5, whose conically running outer surface 6 is configured to be complementary to a conically running inner surface 7 of a conically running recess 8 of the conical cap 4 in such a manner that the conical cap 4 can be placed on the section 5 and receives this at least in some areas.

The section 5 is configured as a truncated cone. The recess 8 has a cavity which is configured as a truncated cone.

The inner surface 7 of the conical cap 4 and the outer surface 6 of the abutment post 2 are inclined relative to one another in such a manner that the conical cap 4 can be connected to the abutment post 2 by a frictional locking between the inner surface 7 and the outer surface 6 in a tension-resistant and captive and safe-to-chew manner.

The conicity of the section 5 differs from the conicity of the recess 8. Conicity is understood as a measure of the change in the diameter of a cone along its axis of symmetry 21, 22.

The conical cap 4 is exclusively connected to the abutment post 2 by frictional locking in a tension-resistant and captive and safe-to-chew manner, wherein no means are provided which connect the conical cap 4 to the abutment post 2 by an adhesive bond and/or form fit in a tension-resistant manner. In particular, no cement is provided and no screws are provided.

The conically running outer surface 6 encloses a first angle of inclination in the amount of 5.8° with the axis of symmetry 21 of its conicity. The conically tapering inner surface 7 encloses a second angle of inclination with the axis of symmetry 22 of its conicity which is greater than the first angle of inclination.

In FIGS. 3 and 4 the axis of symmetry 21 of the conicity of the outer surface 6 is shown as an example. The first angle of inclination which is enclosed by the outer surface 6 with the axis of symmetry 21 is shown. For the sake of clarity, the only slightly larger second angle of inclination is not shown.

The second angle of inclination is about 0.5° larger than the first angle of inclination. The axis of symmetry 22 of the conicity of the inner surface 7 coincides with the other axis of symmetry 21 when the cap 4, 4' is placed as intended on the abutment post 2.

The frictional locking takes place in a lower region of the conical cap 4, 4' that faces the opening 9 of the conical cap 4. The frictional locking takes place by a surface contact.

The frictional locking between the abutment post 2 and the conical cap 4, 4' can be released by a tensile force measuring 30 N.

A first lateral force locking device 10 is provided on the abutment post 2, and a second lateral force locking device 11 is provided in the conical cap 4, 4'.

The first lateral force locking device 10 is configured as a circular cylindrical connector with a free upper end. The connector rests on a plateau, specifically the upper base area 20 of a multi-sided or polygonal prism. The base area 20 is shown in FIG. 2.

The second lateral force locking device 11 is configured as a circular cylindrical cavity with a closed upper end. In the assembled state, the inner wall of the cylindrical cavity can be supported on the shell surface, specifically the laterally outer surface, of the connector. The connector and cavity are arranged coaxially. This prevents any tilting of the conical cap 4, 4'.

A first anti-twisting device 12 is provided on the abutment post 2, and a second anti-twisting device 13 is provided in the conical cap 4, 4'.

FIG. 2 shows that the first anti-twisting device 12 is configured as a multi-sided or polygonal prism. The prism rests on the upper base area 17 of the section 5 which is configured as a truncated cone.

The prism has six edges and six lateral surfaces 18, 19. Three equally large longer lateral surfaces 18 and three equally large shorter lateral surfaces 19 each are provided.

A different number of lateral surfaces could also be provided, which could be different or the same in their dimensions. For example, it is conceivable to form a hexagon.

A longer lateral surface 18 is followed by a shorter lateral surface 19 along the circumference of the prism. The lateral surfaces 18, 19 alternate along the circumference.

The second anti-twisting device 13 is configured as a multi-sided or polygonal prismatic cavity. In the assembled state, the inner wall of the multi-sided or polygonal cavity can abut against the shell surface, specifically the lateral surfaces 18, 19 of the prism. This prevents the conical cap 4 from twisting relative to the abutment post 2.

FIG. 4 shows that on its tip a conical cap 4' has a solid pin 14 that protrudes from the tip. This pin 14 can be joined with a welding wire if several conical caps 4' are to be joined together by means of a welding wire.

The conical cap 4, 4' has only one opening 9, specifically for receiving the abutment post 2.

In addition, the conical cap 4, 4' has an external thread 16. As a result, structures can be arranged on the conical cap 4, 4'.

The conical cap 4, 4' can also have a laterally protruding opening edge which borders the opening 9, but is not depicted here.

With reference to FIG. 5, it is explained how a patient is preferably treated:

Firstly a single implant 1 or the three depicted implants 1 are positioned in the jawbone of the patient using conventional means. It is also conceivable to use only two or more than three implants 1.

The abutment post 2 or abutment posts 2 are then installed, in particular by screwing with the implant 1 or implants 1.

The conical cap 4, 4' or conical caps 4, 4' are then placed on the upper part of the abutment post 2 or the abutment posts 2.

This is followed by applying a pulse or force to the conical cap 4, 4' or the conical caps 4, 4', so as to move the latter into the correct seat.

A welding wire can then be fastened to the pins 14 of several conical caps 4'.

However, it is specifically shown in FIG. 5 that an artificial tooth 3 is joined immediately with a single conical cap 4, in particular by polymerization.

The tooth 3 can be adhesively bonded and/or cemented to the conical cap 4, so that the tooth 3 reveals no visible connecting means, such as screws or injection openings for cement.

The step of placing several artificial teeth 3 can take place after welding of the aforementioned welding wire.

The person skilled in the art also refers to the abutment post using the English term abutment.

Figure 6:
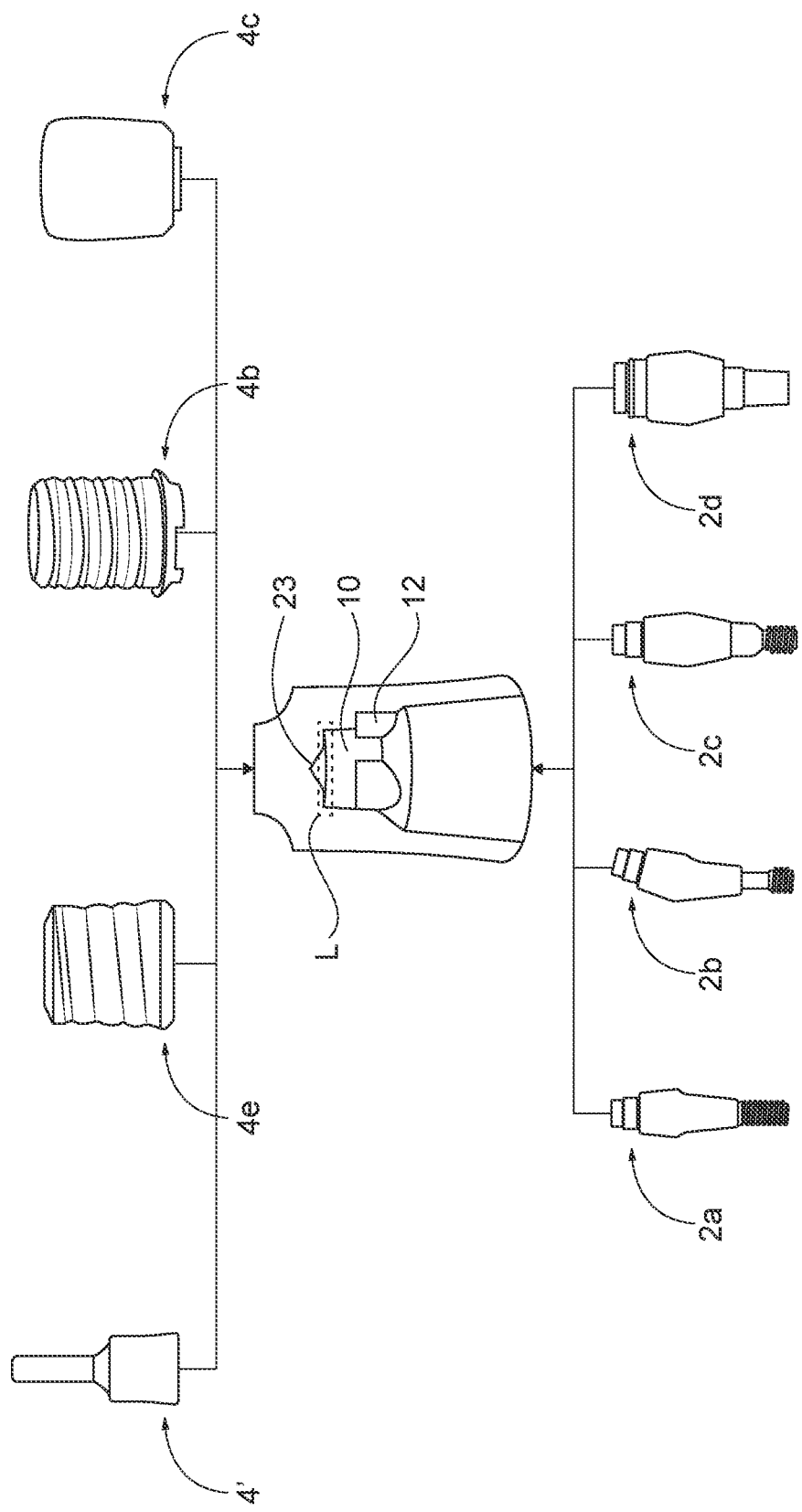
FIG. 6 shows a schematic view of various conical caps which can be placed on different abutment posts to form an arrangement described here, various possible combinations are shown schematically.

FIG. 6 shows by means of variously configured conical caps 4', 4e, 4b, 4c the possibility of freely combining the said conical caps 4', 4e, 4b, 4c with variously configured abutment posts 2a-d with communicating indexing elements between respective conical cap 4', 4e, 4b, 4c and respective abutment post 2a-d.

Shown in the middle of FIG. 6 for example for all the abutment posts shown here is the upper part of a randomly selected abutment post 2a-d which has the said first anti-twisting device 12 and the said first lateral force locking device 10.

Between the respective conical cap 4', 4e, 4b, 4c and the respective abutment post 2a-d there is no gap L such as could occur in the prior art arrangements.

A stop 23 and no gap L is formed axially between the conical cap 4', 4e, 4b, 4c and the abutment post 2a-d.

The conical cap 4', 4e, 4b, 4c comes to rest axially with its inner wall on the stop 23.

The stop 23 is specifically configured here as a cone with a tip or as a tip. The inner wall therefore comes to rest on the tip.

The tip or the cone is arranged on the distal surface of the first lateral force locking device 10 and projects from there in the direction of the conical cap 4', 4e, 4b, 4c.

The stop 23 can naturally be arranged on all the abutment posts 2, 2a-d although not shown in all the figures.

The same applies to the indexing elements shown in FIGS. 2 to 4 which communicate with the indexing elements of the conical caps or are configured to be complementary to these.

The technical features with the reference numbers 5-13 and 17-20 are suitable as indexing elements individually or in combination.

Figure 7:
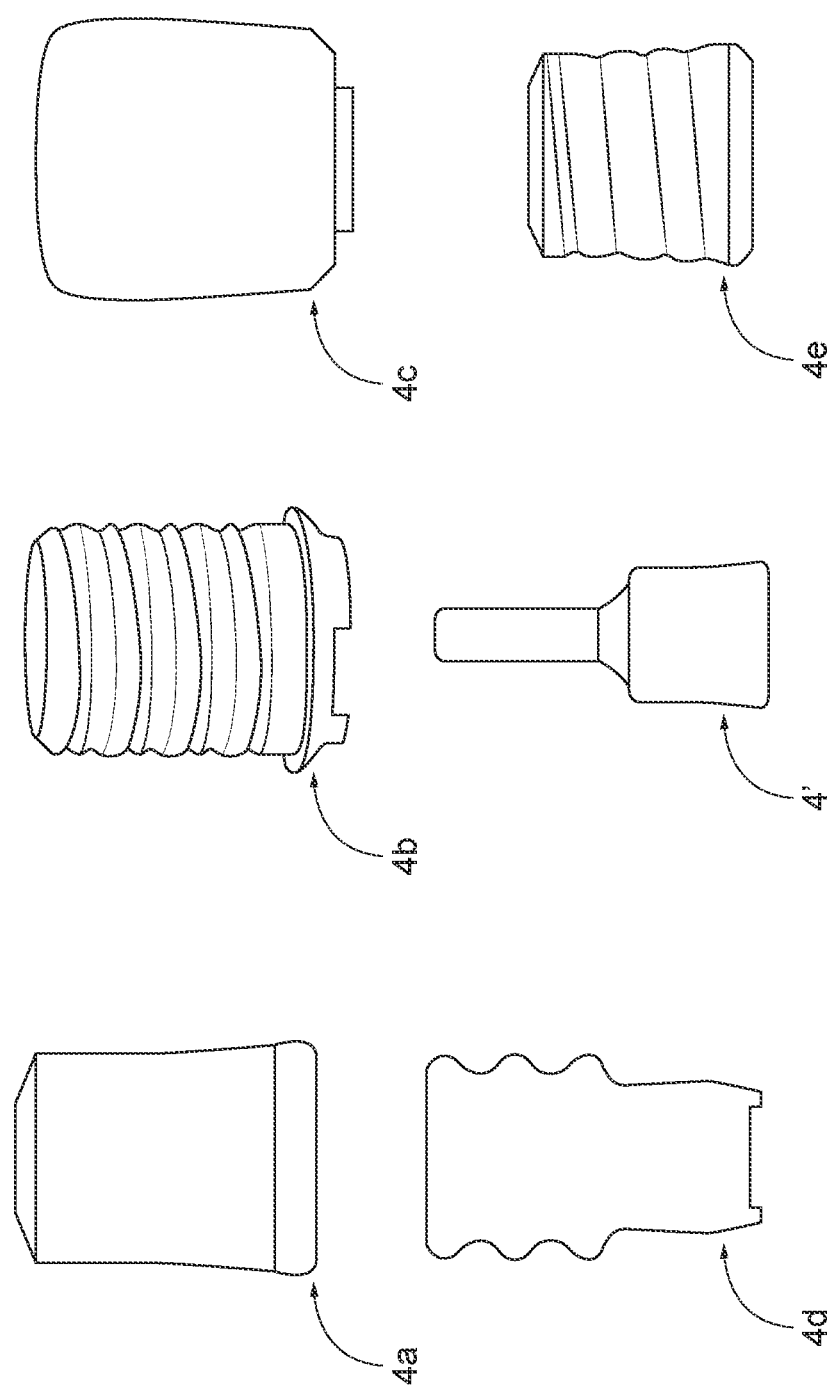
FIG. 7 shows various conical caps.

FIG. 7 shows top left a conical cap 4a which is also designated as laboratory cap. The laboratory cap is used by the dental technician when a crown or bridge is to be made. The laboratory cap can be used for the replacement of an individual tooth or for the replacement of multiple teeth. The laboratory cap has no external retention means. This facilitates the laboratory work. The laboratory cap serves as a place holder for final caps or conical caps. The laboratory cap is only used in the laboratory.

FIG. 7 shows top centre a conical cap 4b which is used as a temporary cap for the replacement of an individual tooth or for the replacement of multiple teeth. The temporary cap is used to construct a temporary, namely preliminary crown or bridge which the patient can use for up to six months. It is a cost-effective solution which can be used in practice to construct a crown or bridge. The temporary cap has a suitable snap-in device or snap-in function which makes it easier to place or remove the temporary cap.

FIG. 7 shows top right a conical cap 4c which is used as a healing cap. The healing cap provides protection for the abutment post when a temporary crown or bridge is not used. The healing cap is used when there is no aesthetic need to close a gap by a tooth-like structure. The patient can use the healing cap for up to six months.

FIG. 7 shows bottom left a conical cap 4d which is also designated as an impression cap or imprint cap. The impression cap can be used for the replacement of an individual tooth or for the replacement of multiple teeth. The impression cap is used to transfer the position of an abutment post to a model which uses an impression.

FIG. 7 shows bottom centre the conical cap 4' which is also designated as weld wire cap. The weld wire cap is made of titanium and is suitable for the replacement of an individual tooth or for the replacement of multiple teeth. The weld wire cap is used to fabricate a durable and temporary prosthetic structure which is based on conical retention means. Weld wire caps as a multiple unit can be used for intra-oral welding. The durable and temporary prosthetic structures are provided to be replaced by final structures which comprise final caps or conical caps.

FIG. 7 shows bottom right the conical cap 4e which is designated as final cap. The final cap is suitable for the replacement of an individual tooth or for the replacement of multiple teeth. The final cap is cemented with the crown or bridge and comprises conical retention means for the structures.

Figure 8:
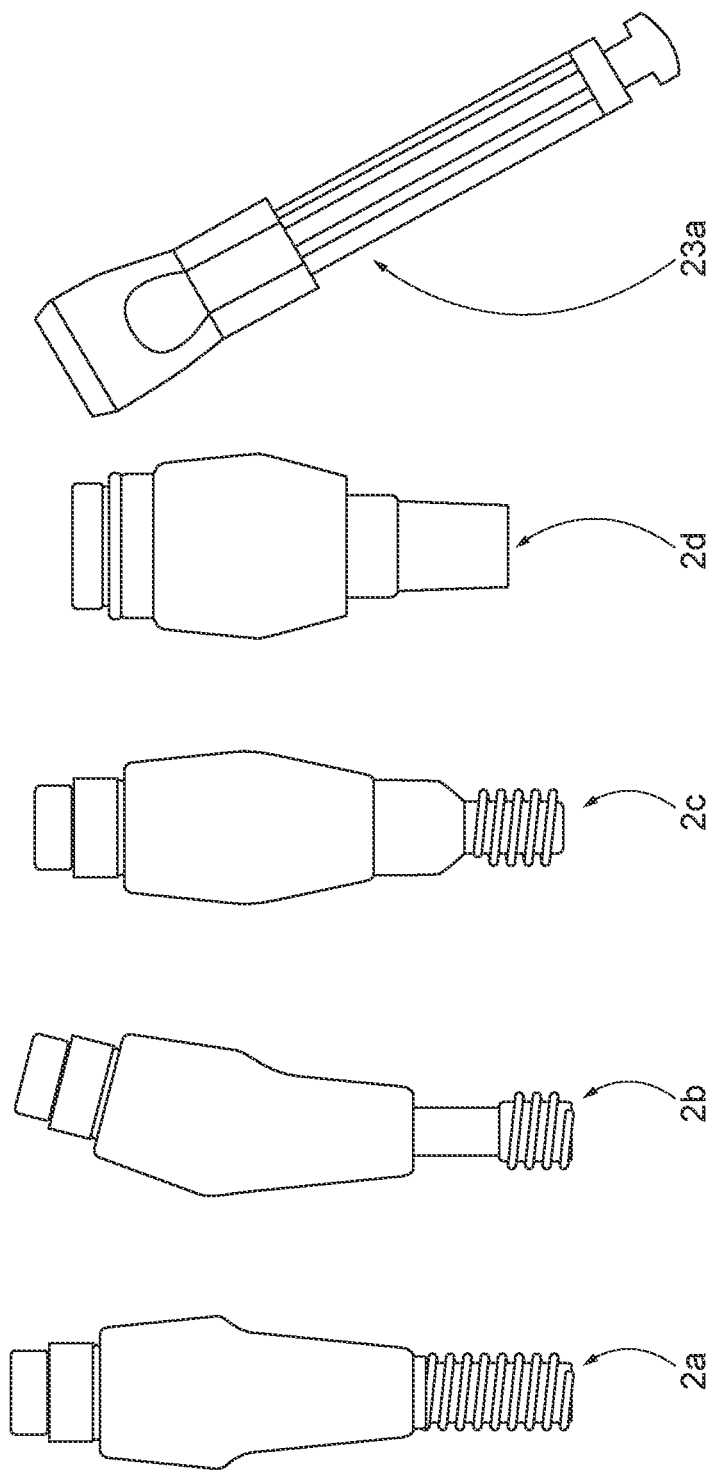
FIG. 8 shows on the left-hand side various abutment posts and on the right-hand side an abutment tool.

FIG. 8 shows various abutment posts 2a-d and on the right an abutment tool 23a. The abutment post 2b shows for example a specific angulation, namely an angled upper part.

All the caps, conical caps and abutment posts shown here can be used in the arrangement described here according to the disclosure.

Figure 9:
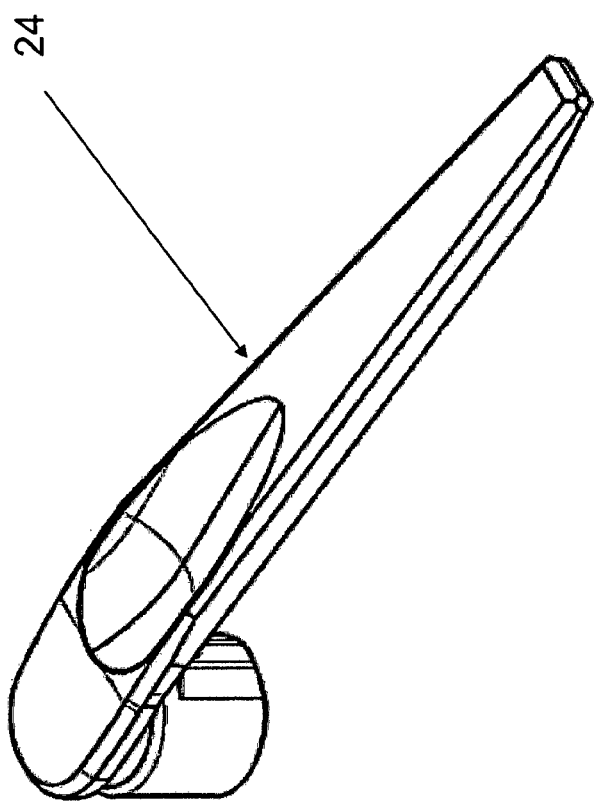
FIG. 9 shows an overall view of a tool for applying a conical cap to an abutment post.

FIG. 9 shows a tool 24 for application of a conical cap of the type described here to an abutment post of the type described here.

Figure 10:
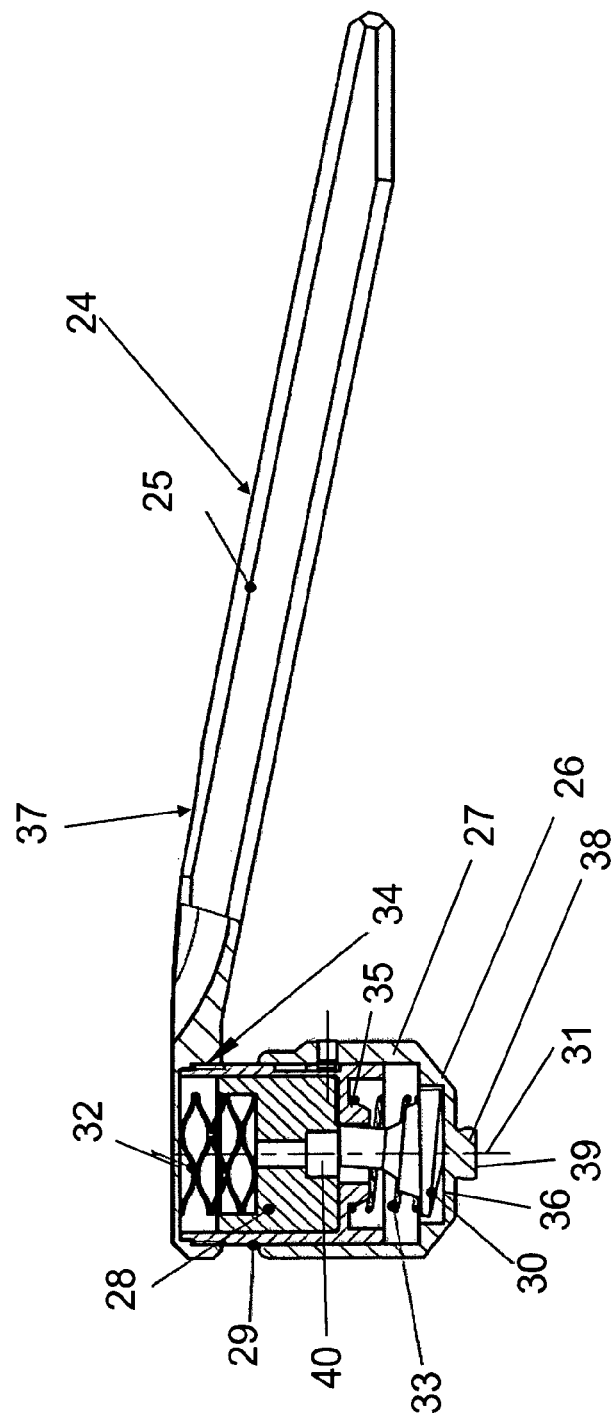
FIG. 10 shows a sectional view of the tool according to FIG. 9 from which the design structure of the tool can be seen.

FIG. 10 shows a tool 24 for application of a conical cap to an abutment post comprising a handle 25 for holding the tool 24 and a device 26 for applying a force or an impulse to the conical cap.

The device 26 comprises a flat striking surface 39 for abutting against the conical cap in order to produce a frictional locking between the conical cap and the abutment post so that these can be joined together in a tension-resistant and/or captive and/or safe-to-chew manner. The striking surface 39 is configured not to be pointed in the direction of the conical cap.

The striking surface 39 is assigned to a striking element 27 of the device 26 wherein the striking element 27 is movable relative to a housing 29 and to the handle 25 in order to initially tension at least one spring 32, 33 and release it again by further movement.

The striking element 27 has a striking connector 38 which projects from the striking element 27 in the direction of the conical cap and has a smaller diameter than the upper part of the striking element 27. The impulse or the force is concentrated in the striking connector 38.

A nutating element 30 is provided which is tiltable relative to the longitudinal axis 31 of the device 26 and with respect to the direction of movement of a spring-loaded hammer 28 and the striking element 27 in order to move the hammer 28 initially against the force of a first spring 32 during movement of the striking element 27.

To this end the striking element 27 is pressed in the direction of the handle 25. The nutating element 30 thereby also presses the hammer 28 in the direction of the handle 25 and thereby tensions the first spring 32. The nutating element 30 is however aligned during the further movement of the striking element 27 in the direction of the handle 25 parallel to the longitudinal axis 31.

When aligned parallel to the longitudinal axis 31 or to the direction of movement, the nutating element 30 dips into a recess 40 of the hammer 28. The first spring 32 is thereby triggered in such a manner that this moves the hammer 28 in the direction of the striking surface 39.

The first spring 32 is provided between the handle 25, here specifically between an inner side of the handle 25 in which the housing 29 is screwed, and the hammer 28.

A second spring 33 is provided for the spring loading of the nutating element 30. The first spring 32 is configured as a corrugated spring. The second spring 33 is configured as a spiral spring.

The housing 29 is screwed hand tight at a screw position 34 with the handle 25, wherein about 4 Nm are used. The housing 29 is ultimately configured to be substantially cylindrical in the direction of the handle 25 and open at the top so that the first spring 32 can be supported against the handle 25.

The housing 29 has a base 35 on which the hammer 28 can be placed or against which the hammer 28 strikes when the first spring 32 is released. The hammer 28 is therefore movable relative to the housing 29 and guided in this in a telescopic manner.

On the side of the base 35 opposite the hammer 28 the second spring 33 is supported with one end. It is supported with the other end on the nutating element 30. The nutating element 30 grips through an opening in the base 35 with a dome so that the dome can dip into the recess 40 in the hammer 28. The nutating element 30 abuts against an inner base 36 of the striking element 27. The inner base 36 is the lower region of a recessed hole or a blind hole.

FIG. 10 shows that the tool 24 has a relatively long handle 25 and a pot-like head which projects from this at the end, namely the device 26. The handle 25 tapers in the direction of the end which faces away from the end of the head. A hollow 37 is formed in the handle 25.

The invention claimed is:

1. An arrangement for positioning in and/or on an implant comprising:
   an abutment post connected to a conical cap, the abutment post having a first anti-twisting device and the conical cap having a second anti-twisting device, the first and second anti-twisting devices being engageable with each other to prevent the conical cap from twisting or rotating relative to the abutment post,
   wherein the abutment post has a conical section with a conical outer surface configured to be complementary to a conical inner surface of a conical recess of the conical cap in such a manner that the conical cap can be placed on the conical section so as to at least partially receive the conical section in its conical recess,
   wherein the inner surface of the conical cap and the outer surface of the abutment post are inclined relative to one another in such a manner that the conical cap can be connected to the abutment post by a friction locking between the inner surface and the outer surface in a tension-resistant and/or captive and/or safe-to-chew manner,
   wherein the conicity of the conical section differs from the conicity of the conical recess,
   wherein the first anti-twisting device comprises a multi-sided or polygonal prism, which rests on an upper base area of the conical section of the abutment post, the conical section being configured as a truncated cone,
wherein the conical cap has only one opening, the only one opening receiving the abutment post,
wherein a first lateral force locking device is provided on the abutment post and a second lateral force locking device is provided in and/or on the conical cap, the first lateral force locking device comprising a cylindrical body that is joined to a top plateau of the prism and has a free upper end, and the second lateral force locking device comprising a cylindrical cavity with a closed upper end, the cylindrical cavity being configured to receive the cylindrical body, whereby the first lateral force locking device and the second lateral force locking device cooperate to prevent the conical cap from tilting relative to a longitudinal axis of the abutment post when a lateral force acts on the conical cap.

2. The arrangement according to claim 1, wherein the conical cap is connected exclusively by frictional locking to the abutment post in a tension-resistant and/or captive and/or safe-to-chew manner, wherein the conical cap is not connected to the abutment post by an adhesive bond and/or form fit in a tension-resistant manner.

3. The arrangement according to claim 1, wherein the conical outer surface encloses with the axis of symmetry of its conicity a first angle of inclination in the range of 1° to 8° that the conical inner surface encloses with the axis of symmetry of its conicity a second angle of inclination in the range of 1° to 8°, wherein the first angle of inclination is greater than or smaller than the second angle of inclination.

4. The arrangement according to claim 3, wherein the first angle of inclination is 5.8°.

5. The arrangement according to claim 1, wherein the frictional locking between the abutment post and the conical cap takes place in a lower region of the conical cap which faces the only one opening of the conical cap.

6. The arrangement according to claim 1, wherein the frictional locking between the abutment post and the conical cap can be released by a tensile force which lies in the range of 2 N to 80 N.

7. The arrangement according to claim 6, wherein the frictional locking between the abutment post and the conical cap can be released by a tensile force in the amount of 30 N.

8. The arrangement according to claim 1, wherein the second anti-twisting device comprises a multi-sided or polygonal cavity.

9. The arrangement according to claim 1, wherein the conical cap has a tip with a solid pin projecting therefrom.

10. The arrangement according to claim 1, wherein the conical cap has an external thread.

11. The arrangement according to claim 1, wherein a stop is located axially between the conical cap and the abutment post.

12. The arrangement according to claim 11, wherein the stop is part of the abutment post or part of the conical cap.

13. A set comprising the arrangement according to claim 1 and a tool for connecting the conical cap to the abutment post, the tool comprising a handle for holding the tool and a device for applying a force to the conical cap, wherein the device comprises striking surface for abutment against the conical cap in order to produce a friction locking between the conical cap and the abutment post, so that the conical cap and the abutment post are connected to one another in a tension-resistant and/or captive and/or safe-to-chew manner.

14. The set according to claim 13, wherein the striking surface is configured to be not pointed in the direction of the conical cap.

15. The set according to claim 13, wherein the striking surface is part of a striking element of the device, wherein the striking element is movable relative to a housing and/or to the handle in order to initially tension at least one spring and release it again by further movement.

16. The set according to claim 15, wherein a nutating element is provided which is tiltable relative to a longitudinal axis of the device and/or the striking element in order to move a hammer initially against the force of a first spring during movement of the striking element.

17. The set according to claim 16, wherein when aligned parallel to the longitudinal axis or to the direction of movement, the nutating element dips into a recess of the hammer and thereby releases the first spring in such a manner as to move the hammer in the direction of the striking surface.

18. The set according to claim 17, wherein the first spring is disposed between the handle and the hammer and wherein a second spring spring-loads the nutating element.

* * * * *